United States Patent
Gomyo et al.

(10) Patent No.: US 11,227,709 B2
(45) Date of Patent: Jan. 18, 2022

(54) SUPERCONDUCTING MAGNET

(71) Applicant: Mitsubishi Electric Corporation, Tokyo (JP)

(72) Inventors: Taisaku Gomyo, Tokyo (JP); Naoki Iwamoto, Tokyo (JP); Tatsuya Inoue, Tokyo (JP); Tomonori Tanaka, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 17/051,178

(22) PCT Filed: Feb. 5, 2019

(86) PCT No.: PCT/JP2019/003969
§ 371 (c)(1),
(2) Date: Oct. 28, 2020

(87) PCT Pub. No.: WO2020/003579
PCT Pub. Date: Jan. 2, 2020

(65) Prior Publication Data
US 2021/0233691 A1    Jul. 29, 2021

(30) Foreign Application Priority Data
Jun. 27, 2018    (JP) .............................. JP2018-121649

(51) Int. Cl.
*H01F 6/04* (2006.01)
*H01F 6/06* (2006.01)

(52) U.S. Cl.
CPC ................ *H01F 6/04* (2013.01); *H01F 6/06* (2013.01)

(58) Field of Classification Search
CPC ... H01F 6/04; H01F 6/06; H01L 39/04; A61B 5/055
See application file for complete search history.

(56) References Cited

U.S. PATENT DOCUMENTS

| 2016/0233011 A1* | 8/2016 | Eguchi ...................... H01F 6/06 |
| 2017/0038123 A1 | 2/2017 | Strickland et al. |
| 2018/0040402 A1 | 2/2018 | Eguchi et al. |

FOREIGN PATENT DOCUMENTS

| JP | 6-163251 A | 6/1994 |
| JP | 5868562 B1 | 2/2016 |
| JP | 2017-511463 A | 4/2017 |

OTHER PUBLICATIONS ip.com Search Results.*
Global Dossier.*
International Search Report and Written Opinion dated Apr. 23, 2019 for PCT/JP2019/003969 filed on Feb. 5, 2019, 7 pages including English Translation of the International Search Report.

* cited by examiner

*Primary Examiner* — Mohamad A Musleh
(74) *Attorney, Agent, or Firm* — Xsensus LLP

(57) ABSTRACT

A superconducting magnet includes a superconducting coil, a coolant container, a radiation shield, a first pipe, a second pipe, a refrigerator, and a connection pipe. The refrigerator is fixed to seal a tip end of the second pipe, and is inserted in the second pipe to define a flow path of a coolant between the refrigerator and the second pipe. The connection pipe makes the interiors of the first pipe and the second pipe communicate with each other inside a vacuum container. The connection pipe includes a first connection portion connecting to the first pipe and a second connection portion connecting to the second pipe. The second connection portion is located between the vacuum container and the radiation shield.

7 Claims, 9 Drawing Sheets

SUPERCONDUCTING MAGNET

CROSS-REFERENCE TO RELATED APPLICATIONS

The present application is based on PCT filing PCT/JP2019/003969, filed Feb. 5, 2019, which claims priority to JP 2018-121649, filed Jun. 27, 2018, the entire contents of each are incorporated herein by reference.

TECHNICAL FIELD

The present invention relates to a superconducting magnet.

BACKGROUND ART

One of the prior documents that disclose the configuration of a superconducting magnet is Japanese Patent No. 5868562 (PTL 1). The superconducting magnet described in PTL 1 includes a superconducting coil, a coolant container, a radiation shield, a vacuum container, a refrigerator, a first exhaust pipe, and a first pressure release valve. The refrigerator is inserted in a cylinder extending from the vacuum container to the coolant container. A first refrigeration stage of the refrigerator is indirectly in contact with the radiation shield. A second refrigeration stage of the refrigerator lies in the upper part in the coolant container and re-liquefies vaporized helium gas.

CITATION LIST

Patent Literature

PTL 1: Japanese Patent No. 5868562

SUMMARY OF INVENTION

Technical Problem

In a typical superconducting magnet, heat that has entered a coolant container due to heat conduction through a pipe connected to the coolant container and radiation from a radiation shield is dissipated to the outside of the coolant container. A refrigerator is therefore continuously operated during working of the superconducting magnet, resulting in an increase in power consumption.

Performing an intermittent operation in which a refrigerator is repeatedly operated and stopped is one method for reducing power consumption of the refrigerator. When performing the intermittent operation of a refrigerator, the operating time of the refrigerator can be reduced as the time required for pressure increase in a coolant container at the time of stop of the refrigerator increases, and as the time required for pressure decrease in the coolant container at the time of restart of operation of the refrigerator decreases.

To increase the time required for pressure increase in the coolant container at the time of stop of the refrigerator, an amount of heat entering the coolant container needs to be reduced. To reduce the time required for pressure decrease in the coolant container at the time of restart of operation of the refrigerator, cooling efficiency in the coolant container needs to be improved.

The present invention has been made in view of the above problem, and aims to provide a superconducting magnet in which power consumption of a refrigerator can be reduced by reducing an amount of heat entering a coolant container and improving cooling efficiency in the coolant container.

Solution to Problem

A superconducting magnet according to the present invention includes a superconducting coil, a coolant container, a radiation shield, a first pipe, a second pipe, a refrigerator, and a connection pipe. The coolant container contains the superconducting coil and coolant for cooling the superconducting coil. The radiation shield is disposed between the coolant container and a vacuum container containing the coolant container, to surround the coolant container. The first pipe is connected to the coolant container from outside of the vacuum container. The second pipe is connected to the coolant container from outside of the vacuum container. The refrigerator is fixed to seal a tip end of the second pipe, and is inserted in the second pipe to define a flow path of the coolant between the refrigerator and the second pipe. The connection pipe makes an interior of the first pipe and an interior of the second pipe communicate with each other inside the vacuum container. The connection pipe includes a first connection portion connecting to the first pipe and a second connection portion connecting to the second pipe. The second connection portion is located between the vacuum container and the radiation shield.

Advantageous Effects of Invention

According to the present invention, since the interior of the first pipe and the interior of the second pipe communicate with each other through the connection pipe, a circulating flow in which the coolant naturally circulates due to a density difference can be generated. The coolant is cooled when this circulating flow is passing through the flow path defined between the refrigerator and the second pipe, and accordingly cooling efficiency in the coolant container can be improved. Further, since the coolant passes through each of the first pipe and the second pipe, the entry of heat into the coolant container by heat conduction through each of the first pipe and the second pipe can be suppressed. This, in turn, can reduce power consumption of the refrigerator in the superconducting magnet.

DESCRIPTION OF EMBODIMENTS

Hereinafter superconducting magnets according to embodiments of the present invention are described with reference to the figures. In the description of the embodiments below, identical or equivalent parts are identically denoted in the figures and explanations thereof are not repeated. Note that although a description of a cylindrical superconducting magnet is given in the following embodiments, the present invention is not necessarily limited to a cylindrical superconducting magnet but may also be applied to an open superconducting magnet.

First Embodiment

Figure 1:
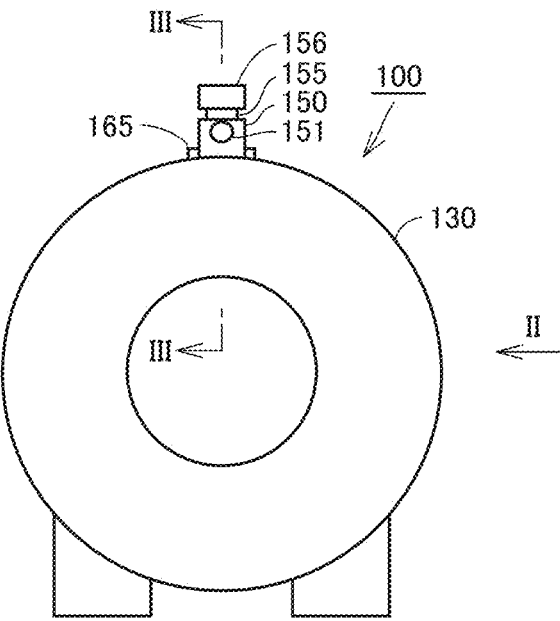
FIG. 1 is a front view showing a superconducting magnet according to a first embodiment of the present invention.
Figure 2:
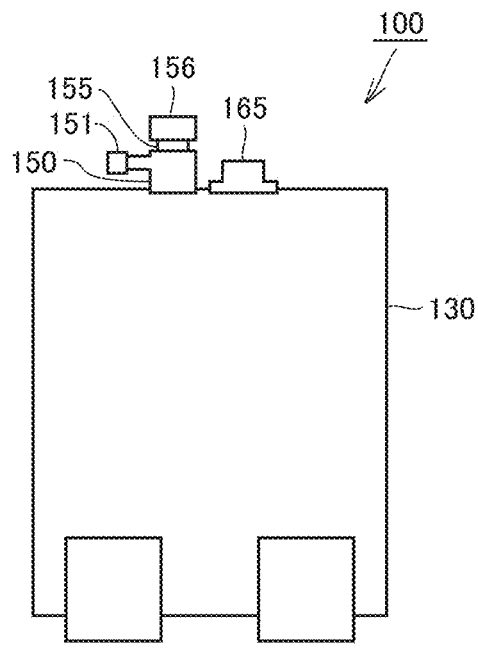
FIG. 2 is a side view of the superconducting magnet in FIG. 1 as seen from a direction of an arrow II.
Figure 3:
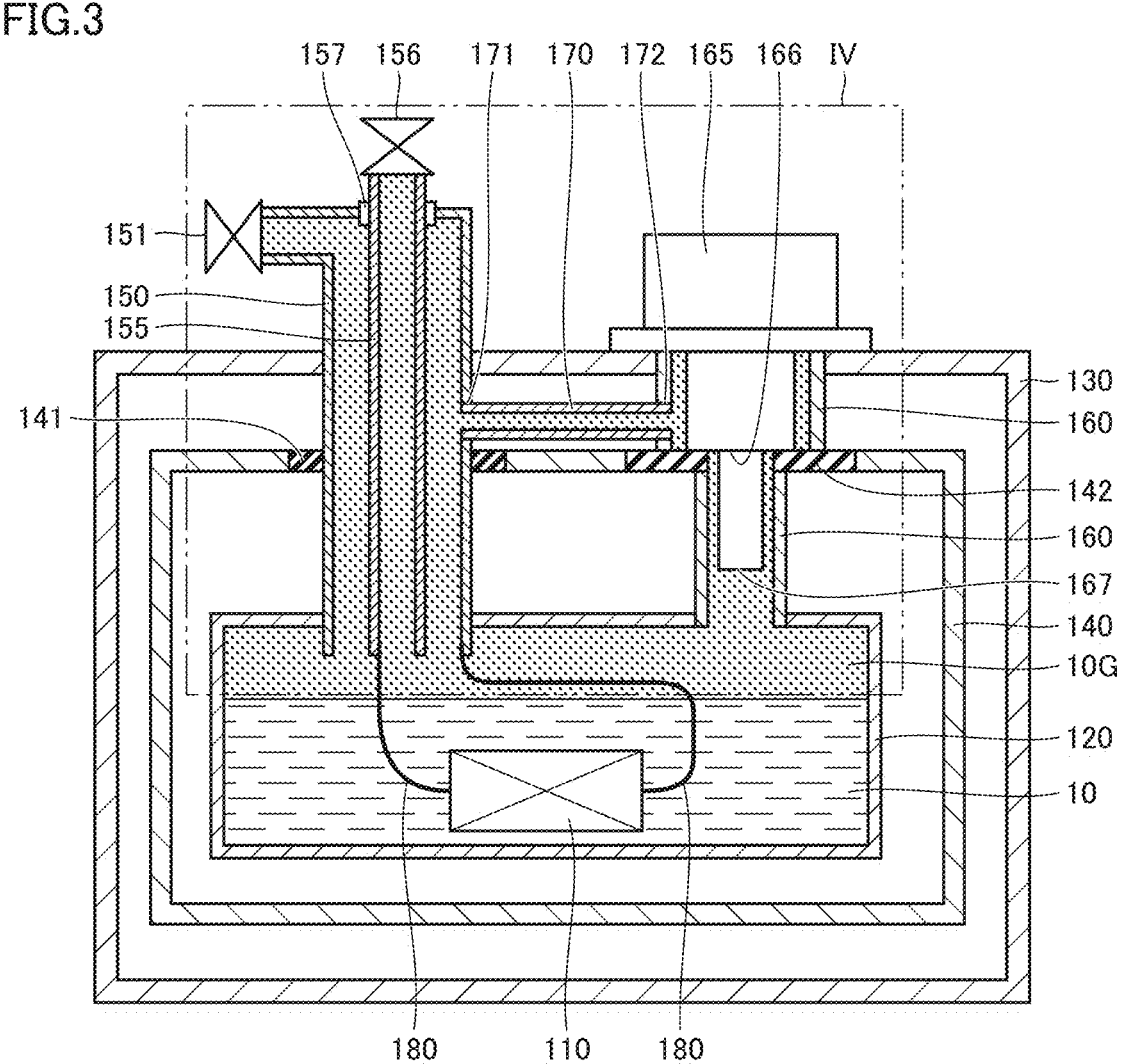
FIG. 3 is a cross-sectional view of the superconducting magnet in FIG. 1 as seen from a direction of arrows of line III-III.

FIG. 1 is a front view showing a superconducting magnet according to a first embodiment of the present invention. FIG. 2 is a side view of the superconducting magnet in FIG. 1 as seen from a direction of an arrow II. FIG. 3 is across-sectional view of the superconducting magnet in FIG. 1 as seen from a direction of arrows of line III-III. FIG. 3 shows a cross section of only the upper part of the superconducting magnet. In FIGS. 1 to 3, the components are shown in a simplified form for the sake of simplicity.

As shown in FIGS. 1 to 3, a superconducting magnet 100 according to the first embodiment includes a superconducting coil 110, a coolant container 120, a vacuum container 130, a radiation shield 140, a first pipe 150, a first pressure release valve 151, a second pipe 160, a refrigerator 165, a third pipe 155, a second pressure release valve 156, and a connection pipe 170. Note that superconducting magnet 100 does not necessarily have to include third pipe 155 and second pressure release valve 156. If superconducting magnet 100 does not include third pipe 155 and second pressure release valve 156, an electrode bar inserted from outside of vacuum container 130 or the like may be used as an electrode which will be described later.

Coolant container 120 contains superconducting coil 110 and coolant for cooling superconducting coil 110. In the present embodiment, coolant container 120 contains superconducting coil 110 in a state where the superconducting coil is immersed in a liquid coolant 10. Liquid coolant 10 is liquid helium in the present embodiment, but may be liquid nitrogen or the like. A part in coolant container 120 other than superconducting coil 110 and liquid coolant 10 is filled with a vaporized coolant 10G. If liquid coolant 10 is liquid helium, coolant container 120 functions as a cryostat for keeping superconducting coil 110 at a cryogenic temperature of 5 K or less.

Coolant container 120 is provided with two openings to make the interior and the exterior of coolant container 120 communicate with each other. First pipe 150 is connected to one of the openings, and second pipe 160 is connected to the other opening. Coolant container 120 is made of stainless steel, for example.

Vacuum container 130 contains coolant container 120. Vacuum container 130 has a hollow cylindrical shape that is substantially similar to the outer shape of coolant container 120. Vacuum container 130 is provided with two openings at positions corresponding to the two openings in coolant container 120. The interior of vacuum container 130 is reduced in pressure to a high vacuum state in order to improve heat insulation of coolant container 120. More specifically, apart from inside of vacuum container 130 to outside of coolant container 120 is reduced in pressure to a high vacuum state. Vacuum container 130 is made of stainless steel, for example.

Radiation shield 140 is disposed between coolant container 120 and vacuum container 130, to surround coolant container 120. Radiation shield 140 has a hollow cylindrical shape that is substantially similar to the shape of coolant container 120. Radiation shield 140 is provided with two openings at positions corresponding to the two openings in coolant container 120. Radiation shield 140 is installed to reduce heat radiation from vacuum container 130 to coolant container 120. Radiation shield 140 is preferably made of a material having a high light reflectance and a high thermal conductivity, and is made of aluminum, for example.

First pipe 150 is connected to coolant container 120 from outside of vacuum container 130. First pipe 150 extends from outside of vacuum container 130 toward coolant container 120 in a radial direction of coolant container 120. First pipe 150 serves as a flow path of vaporized coolant 10G. A first thermal anchor 141 is disposed on an outer circumferential surface of first pipe 150 at a position corresponding to radiation shield 140. First thermal anchor 141 is a block-like member made of a material having a high thermal conductivity such as copper or aluminum. First thermal anchor 141 is connected to one of the openings in radiation shield 140 with a flexible conductor (not shown) interposed therebetween. First pipe ISO is indirectly cooled by a first refrigeration stage of refrigerator 165, which will be described later in detail.

An end of first pipe 150 at the vacuum container 130 side is located outside vacuum container 130. An end of first pipe 150 at the coolant container 120 side is located in coolant container 120 in the present embodiment. The outer circumferential surface of first pipe 150 at the coolant container 120 side is connected to one of the openings provided in coolant container 120. First pipe 150 and coolant container 120 are connected to each other by welding or the like. First pipe 150 and coolant container 120 may be connected to each other with a flange interposed therebetween. The end of first pipe 150 at the coolant container 120 side may be connected to the opening provided in coolant container 120. First pipe 150 is made of stainless steel, for example.

In the present embodiment, first pressure release valve 151 is connected to first pipe 150 outside vacuum container 130. First pressure release valve 151 has the function of preventing an excessive increase in internal pressure of coolant container 120. That is, when the pressure in coolant container 120 increases excessively, first pressure release valve 151 opens to release vaporized coolant 10G in coolant container 120 into the atmosphere.

Second pipe 160 is connected to coolant container 120 from outside of vacuum container 130. Second pipe 160 extends from outside of vacuum container 130 toward coolant container 120 in the radial direction of coolant container 120. In the present embodiment, second pipe 160 has a second thermal anchor 142 at a central portion in a direction in which second pipe 160 extends. Second pipe 160 has different outer diameters, depending on the outer diameter of refrigerator 165, at the coolant container 120 side and at the vacuum container 130 side with respect to second thermal anchor 142.

An end of second pipe 160 at the vacuum container 130 side is located outside vacuum container 130. A flange of refrigerator 165 is fixed to the end of second pipe 160 at the vacuum container 130 side.

On the other hand, an end of second pipe 160 at the coolant container 120 side is connected to the other opening provided in coolant container 120 in the present embodiment. Second pipe 160 and coolant container 120 are connected to each other by welding or the like. Second pipe 160 and coolant container 120 may be connected to each other with a flange interposed therebetween. The end of second pipe 160 at the coolant container 120 side may be located in coolant container 120. In this case, an outer circumferential surface of second pipe 160 at the coolant container 120 side is connected to the other opening provided in coolant container 120.

Superconducting magnet 100 for use in a magnetic imaging device is installed in a room temperature environment such as a hospital examination room. Therefore, heat constantly enters radiation shield 140 from vacuum container 130, and furthermore, heat constantly enters coolant container 120 from radiation shield 140. If vaporized coolant 10G continues to be generated inside coolant container 120 due to the entry of heat into coolant container 120, vaporized coolant 10G increases in amount of substance, causing an increase in internal pressure of coolant container 120. If the internal pressure of coolant container 120 increases too much, coolant container 120 may break, or it may become impossible to maintain superconducting coil 110 in a superconducting state due to an increase in temperature of liquid coolant 10. Thus, refrigerator 165 is installed in superconducting magnet 100 in order to dissipate the heat that has entered coolant container 120 to the outside of coolant container 120.

Refrigerator 165 is fixed to seal a tip end of second pipe 160, and is inserted in second pipe 160 to define a flow path of vaporized coolant 10G between the refrigerator and second pipe 160. The tip end of second pipe 160 is the end of second pipe 160 at the vacuum container 130 side. The flow path of vaporized coolant 10G defined between second pipe 160 and refrigerator 165 will be described later.

In the present embodiment, refrigerator 165 includes a first refrigeration stage 166 and a second refrigeration stage 167. A Gifford-McMahon refrigerator or a pulse tube refrigerator each having such two refrigeration stages is used as refrigerator 165. Refrigerator 165 has a cooling capacity that varies with temperature of each refrigeration stage. First refrigeration stage 166 is provided at a central portion in a longitudinal direction of refrigerator 165, and second refrigeration stage 167 is provided at a tip portion in the longitudinal direction of refrigerator 165.

If liquid helium is used as liquid coolant 10, first refrigeration stage 166 of refrigerator 165 has a temperature of not less than 30 K and not more than 60 K, for example, first refrigeration stage 166 has a cooling capacity of not less than 20 W and not more than 70 W for example, second refrigeration stage 167 has a temperature of 4 K, for example, and second refrigeration stage 167 has a cooling capacity of 1 W, for example.

First refrigeration stage 166 is located in a region between vacuum container 130 and radiation shield 140 inside second pipe 160. Note that the region between vacuum container 130 and radiation shield 140 inside second pipe 160 means a region between vacuum container 130 and radiation shield 140 inside second pipe 160 in the direction in which second pipe 160 extends.

In the present embodiment, first refrigeration stage 166 is located in a region between a second connection portion which will be describe later and radiation shield 140 inside second pipe 160. Note that the region between the second connection portion and radiation shield 140 inside second pipe 160 means a region between the second connection portion and radiation shield 140 inside second pipe 160 in the direction in which second pipe 160 extends.

Second refrigeration stage 167 is located in at least one of a region between radiation shield 140 and coolant container 120 inside second pipe 160, and an upper region inside coolant container 120.

That is, second refrigeration stage 167 may be located in the region between radiation shield 140 and coolant container 120 inside second pipe 160, or may be located in the upper region inside coolant container 120, or may be located in each of the region between radiation shield 140 and coolant container 120 inside second pipe 160 and the upper region inside coolant container 120.

Second thermal anchor 142 is a block-like member made of a material having a high thermal conductivity such as copper or aluminum. Second thermal anchor 142 is connected to the other opening in the radiation shield with a flexible conductor (not shown) interposed therebetween.

First refrigeration stage 166 is directly in contact with second thermal anchor 142, and indirectly cools radiation shield 140 with second thermal anchor 142 interposed therebetween. Radiation shield 140 is indirectly in contact with first thermal anchor 141. Therefore, by cooling radiation shield 140, first pipe 150 can be cooled by heat conduction through first thermal anchor 141. Second refrigeration stage 167 cools vaporized coolant 10G inside coolant container 120.

The flow path of vaporized coolant 10G defined between second pipe 160 and refrigerator 165 is now described. Second thermal anchor 142 or first refrigeration stage 166 is provided with a coolant flow path (not shown) so that vaporized coolant 10G flows through second pipe 160. The coolant flow path may be provided in both second thermal anchor 142 and first refrigeration stage 166.

The coolant flow path may be structured, for example, such that a groove is formed in at least one of second thermal anchor 142 and first refrigeration stage 166 at a portion where second thermal anchor 142 and first refrigeration stage 166 are in contact with each other.

Vaporized coolant 10G in second pipe 160 decreases in temperature toward coolant container 120 by being cooled by refrigerator 165. Vaporized coolant 10G in second pipe 160 increases in density toward coolant container 120.

In the present embodiment, third pipe 155 extends from outside of vacuum container 130 toward coolant container 120. Third pipe 155 at least partially extends along first pipe 150 while being spaced from first pipe 150 inside first pipe 150.

First pipe 150 and third pipe 155 are electrically insulated from each other. Specifically, third pipe 155 is disposed to penetrate first pipe 150, and third pipe 155 is fixed at this penetrating portion to first pipe 150 with an insulating portion 157 interposed therebetween. An end of third pipe 155 at the vacuum container 130 side is located outside vacuum container 130 and first pipe 150. An end of third pipe 155 at the coolant container 120 side is located inside at least one of first pipe 150 and coolant container 120. In the present embodiment, the end of third pipe 155 at the coolant container 120 side is disposed such that it is positioned substantially the same as the end of first pipe 150 at the coolant container 120 side in a direction in which first pipe 150 extends.

Third pipe 155 defines an auxiliary flow path of vaporized coolant 10G. Third pipe 155 is made of stainless steel, for example. Third pipe 155 is also used, together with first pipe 150, as an electrode for passing a current to superconducting coil 110. Each of first pipe 150 and third pipe 155 is connected to superconducting coil 110 through a current lead 180.

In the present embodiment, second pressure release valve 156 is connected to a tip end of third pipe 155 outside of vacuum container 130. The tip end of third pipe 155 is the end of third pipe 155 at the vacuum container 130 side. As with first pressure release valve 151 connected to first pipe 150, second pressure release valve 156 has the function of preventing an excessive increase in internal pressure of coolant container 120.

Connection pipe 170 makes the interior of first pipe 150 and the interior of second pipe 160 communicate with each other inside vacuum container 130. Connection pipe 170 is made of, for example, a material such as stainless steel or aluminum. Connection pipe 170 is a flexible pipe in the present embodiment.

Connection pipe 170 includes a first connection portion 171 connecting to first pipe 150, and a second connection portion 172 connecting to second pipe 160. Second connection portion 172 is located between vacuum container 130 and radiation shield 140. In the present embodiment, first connection portion 171 is also located between vacuum container 130 and radiation shield 140.

Connection pipe 170 is connected at first connection portion 171 to first pipe 150 by welding or the like, so as to prevent leakage of vaporized coolant 10G in first pipe 150. Connection pipe 170 may be connected at first connection portion 171 to first pipe 150 with a flange interposed therebetween.

Connection pipe 170 is connected at second connection portion 172 to second pipe 160 by welding or the like, so as to prevent leakage of vaporized coolant 10G in second pipe 160. Connection pipe 170 may be connected at second connection portion 172 to second pipe 160 with a flange interposed therebetween.

In the present embodiment, connection pipe 170 is entirely, that is, from first connection portion 171 connecting to first pipe 150 to second connection portion 172 connecting to second pipe 160, disposed in a vacuum atmosphere inside vacuum container 130.

Figure 4:
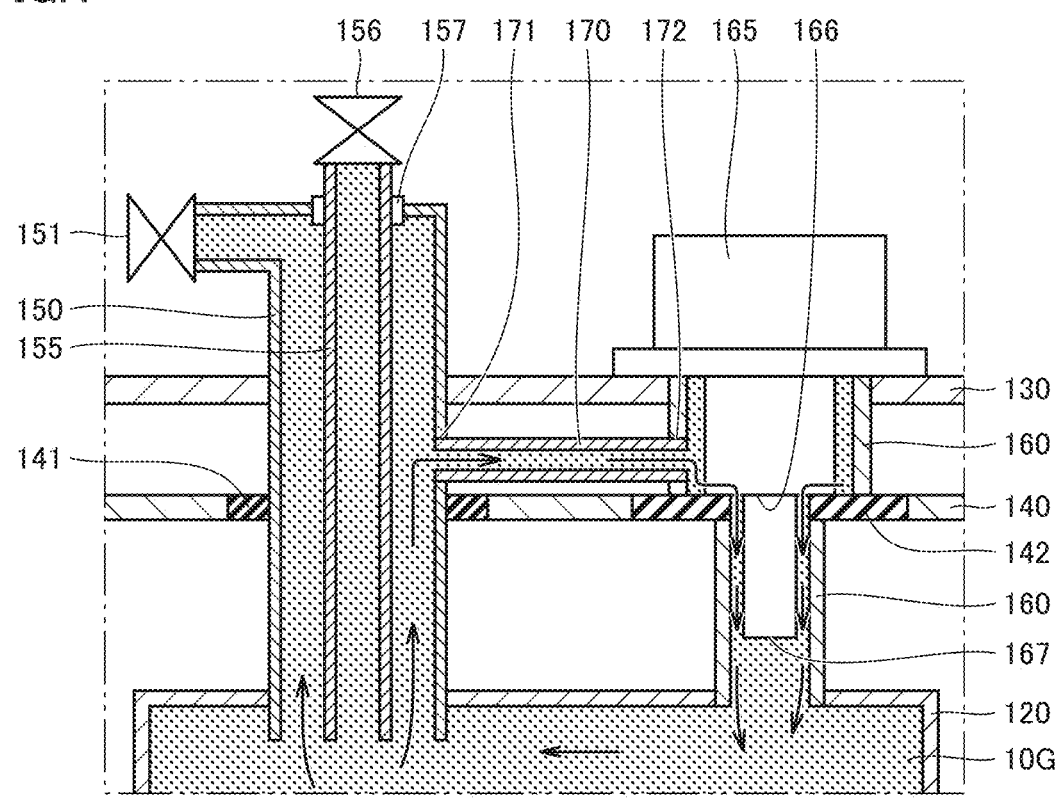
FIG. 4 shows a circulating flow of vaporized coolant, by enlarging a part IV in FIG. 3.

A mechanism that generates a circulating flow in which coolant 10G vaporized in coolant container 120 naturally circulates in superconducting magnet 100 according to the present embodiment is now described with reference to FIG. 4. FIG. 4 shows the circulating flow of the vaporized coolant, by enlarging a part IV in FIG. 3.

First, coolant 10 inside first pipe 150 is heated by heat that has entered from outside of vacuum container 130 through first pipe 150, and increases in temperature. Coolant 10G having the increased temperature decreases in specific gravity and moves upward. As a result, as shown in FIG. 4, an upwardly moving flow of coolant 10G is generated inside first pipe 150.

Coolant 10G that has moved upward inside first pipe 150 flows into connection pipe 170. When flowing from first pipe 150 toward second pipe 160 through connection pipe 170, coolant 10G slightly increases in temperature from the effect of radiant heat from vacuum container 130.

Coolant 10G that has flowed through connection pipe 170 flows into the region between vacuum container 130 and radiation shield 140 inside second pipe 160. In the region between vacuum container 130 and radiation shield 140 inside second pipe 160, first refrigeration stage 166 is also located. Therefore, coolant 10G that has flowed into second pipe 160 from connection pipe 170 is cooled when flowing along first refrigeration stage 166. Cooled coolant 10G increases in specific gravity and moves downward, and therefore passes through the coolant flow path between first refrigeration stage 166 and second pipe 160 and flows toward coolant container 120, thus proceeding to second refrigeration stage 167.

When flowing along second refrigeration stage 167, coolant 10G is further cooled by second refrigeration stage 167, and increases in specific gravity and moves downward. In this manner, a flow of coolant 10G toward coolant container 120 is generated inside second pipe 160.

The generation of the flow of coolant 10G toward coolant container 120 inside second pipe 160 leads to a reduction in internal pressure of the region between vacuum container 130 and radiation shield 140 inside second pipe 160, thus generating a flow in which coolant 10G in connection pipe 170 is drawn into second pipe 160. Further, a flow of coolant 10G from the second pipe 160 side toward first pipe 150 is generated inside coolant container 120.

In this manner, in the present embodiment, the circulating flow in which coolant 10G circulates through coolant container 120, first pipe 150, connection pipe 170, second pipe 160 and coolant container 120 in this order is naturally generated. As a result of the generation of this circulating flow of coolant 10G, each of first pipe 150 and third pipe 155 is cooled by sensible heat of coolant 10G. Accordingly, the entry of heat into coolant container 120 by heat conduction through each of first pipe 150 and third pipe 155 can be suppressed.

This circulating flow can also allow coolant 10G to pas through each of first refrigeration stage 166 and second refrigeration stage 167. First refrigeration stage 166 has a higher cooling capacity than second refrigeration stage 167. In superconducting magnet 100 according to the present embodiment, therefore, a heat load of second refrigeration stage 167 can be reduced to improve cooling efficiency of refrigerator 165, as compared to a conventional superconducting magnet in which coolant is cooled only at second refrigeration stage 167. As a result, cooling efficiency in coolant container 120 can be improved.

Further, since connection pipe 170 is located inside vacuum container 130, the amount of heat entering connection pipe 170 from outside of vacuum container 130 is low. Accordingly, cooling efficiency in coolant container 120 can be effectively improved.

As described above, superconducting magnet 100 according to the present embodiment includes connection pipe 170 to make the interiors of first pipe 150 and second pipe 160 communicate with each other inside vacuum container 130. In addition, refrigerator 165 is inserted in second pipe 160 to define the flow path of coolant 10G between the refrigerator and second pipe 160, and second connection portion 172 connecting connection pipe 170 to second pipe 160 is located between vacuum container 130 and radiation shield 140.

Accordingly, a circulating flow in which coolant 10G vaporized in coolant container 120 naturally circulates due to a density difference can be generated. This circulating flow can cool coolant 10G in the flow path defined between refrigerator 165 and second pipe 160 in second pipe 160, thereby improving cooling efficiency in coolant container 120.

Further, since vaporized coolant 10G passes through each of first pipe 150 and second pipe 160, the entry of heat into coolant container 120 by heat conduction through each of first pipe 150 and second pipe 160 can be suppressed. This, in turn, can reduce power consumption of refrigerator 165 in superconducting magnet 100.

Further, in the present embodiment, first refrigeration stage 166 is located in the region between vacuum container 130 and radiation shield 140 inside second pipe 160, and second refrigeration stage 167 is located in at least one of the region between radiation shield 140 and coolant container 120 inside second pipe 160, and the upper region inside coolant container 120.

This can allow coolant 10G to pass through each of first refrigeration stage 166 and second refrigeration stage 167, thereby reducing a heat load of second refrigeration stage 167 to improve cooling efficiency of refrigerator 165. This, in turn, can improve cooling efficiency in coolant container 120.

Further, in the present embodiment, since first refrigeration stage 166 is located in the region between second connection portion 172 and radiation shield 140 inside second pipe 160, the circulating flow can directly pass through first refrigeration stage 166 to effectively cool coolant 10G at first refrigeration stage 166.

Further, superconducting magnet 100 according to the present embodiment further includes third pipe 155 extending from outside of vacuum container 130 toward coolant container 120 and at least partially extending along first pipe 150 while being spaced from first pipe 150 inside first pipe 150. When the pressure in coolant 10G increases, the tip end of each of first pipe 150 and third pipe 155 can be opened to prevent an excessive increase in internal pressure of coolant container 120.

Note that first refrigeration stage 166 is only required to be located in the region between vacuum container 130 and radiation shield 140 inside second pipe 160, and does not necessarily have to be located in the region between second connection portion 172 and radiation shield 140 inside second pipe 160. That is, first refrigeration stage 166 may be located in a region between vacuum container 130 and second connection portion 172 inside second pipe 160. In this case, too, coolant 10G that has flowed into the region between vacuum container 130 and radiation shield 140 inside second pipe 160 can be cooled by first refrigeration stage 166. Note that the region between vacuum container 130 and second connection portion 172 inside second pipe 160 means a region between vacuum container 130 and second connection portion 172 inside second pipe 160 in the direction in which second pipe 160 extends.

Second Embodiment

A superconducting magnet according to a second embodiment of the present invention is described below. The superconducting magnet according to the second embodiment of the present invention is different from superconducting magnet 100 according to the first embodiment of the present invention only in the configuration of the first pipe. Thus, description of the configuration similar to that of superconducting magnet 100 according to the first embodiment of the present invention will not be repeated.

Figure 5:
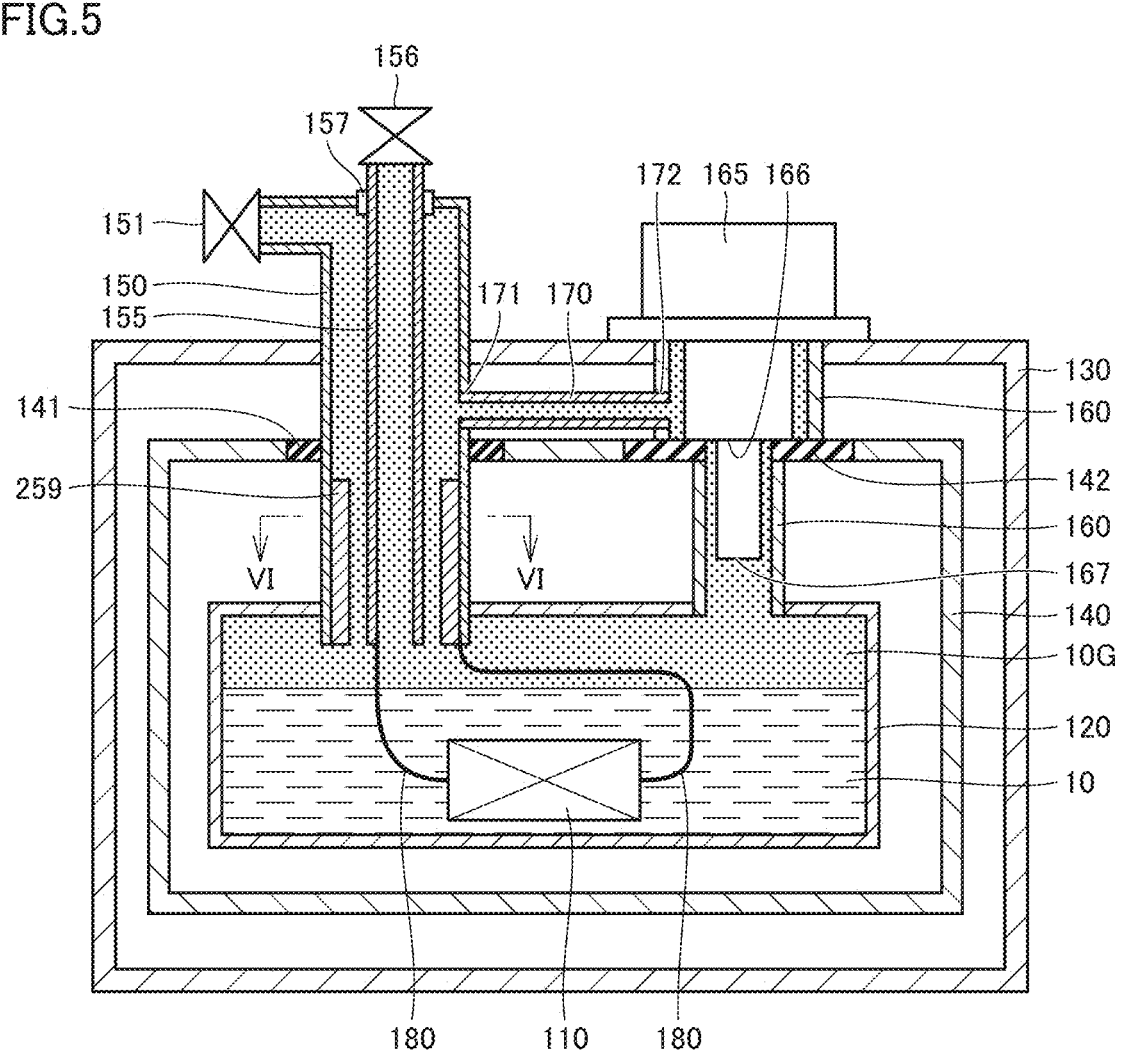
FIG. 5 is a cross-sectional view showing the configuration of a superconducting magnet according to a second embodiment of the present invention.

FIG. 5 is a cross-sectional view showing the configuration of the superconducting magnet according to the second embodiment of the present invention.

Figure 6:
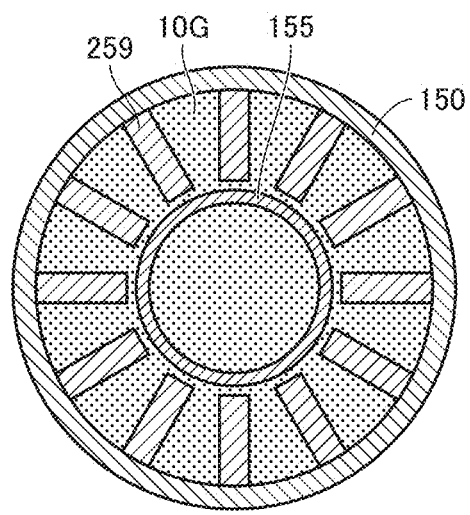
FIG. 6 is a cross-sectional view of the superconducting magnet in FIG. 5 as seen from a direction of arrows of line VI-VI.

FIG. 6 is a cross-sectional view of the superconducting magnet in FIG. 5 as seen from a direction of arrows of line VI-VI. FIG. 5 shows a cross section of only the upper part of the superconducting magnet. In FIG. 5, the components are shown in a simplified form for the sake of simplicity.

The superconducting magnet according to the second embodiment of the present invention further includes, as shown in FIGS. 5 and 6, heat dissipating portions 259 provided on an inner surface of first pipe 150 at the coolant container 120 side with respect to first connection portion 171.

Heat dissipating portions 259 are made of, for example, a material having a high thermal conductivity such as copper or aluminum. As shown in FIG. 6, the superconducting magnet according to the present embodiment includes a plurality of heat dissipating portions 259, which are spaced from one another in a circumferential direction of first pipe 150. The plurality of heat dissipating portions 259 are each spaced from third pipe 155.

When vaporized coolant 10G in first pipe 150 is flowing through a gap between heat dissipating portions 259 and third pipe 155 and gaps between heat dissipating portions 259 by the circulating flow, first pipe 150 exchanges heat with coolant 10G with heat dissipating portions 259 interposed therebetween. As a result, first pipe 150 directly exchanges heat with coolant 10G and indirectly exchanges heat with coolant 10G with heat dissipating portions 259 interposed therebetween, and is thereby cooled. Coolant 10G that has cooled first pipe 150 is cooled at first refrigeration stage 166, to thereby transport sensible heat.

Although not particularly limited, the space between heat dissipating portions 259 and third pipe 155 needs to be such that workability during assembly of the superconducting magnet will not be impaired, and that an insulating distance between first pipe 150 and third pipe 155 can be secured.

Although heat dissipating portions 259 are shaped as fins extending along the direction in which first pipe 150 extends in the present embodiment, the present embodiment is not limited as such.

Figure 7:
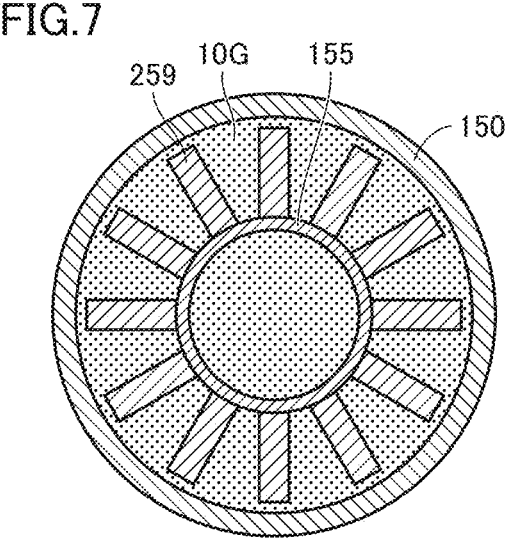
FIG. 7 is a cross-sectional view showing the configuration of a superconducting magnet according to a variation of the second embodiment of the present invention.

FIG. 7 is a cross-sectional view showing the configuration of a superconducting magnet according to a variation of the second embodiment of the present invention. FIG. 7 is shown in the same cross section as FIG. 6.

As shown in FIG. 7, in the superconducting magnet according to the variation of the second embodiment of the present invention, heat dissipating portions 259 are provided on an outer surface of third pipe 155. Note that heat dissipating portions 259 may be provided on each of the inner surface of first pipe 150 and the outer surface of third pipe 155. In this case, heat dissipating portions 259 provided on the outer surface of third pipe 155 are disposed between heat dissipating portions 259 provided on the inner surface of first pipe 150.

In the present variation, when vaporized coolant 10G in first pipe 150 is flowing through a gap between heat dissipating portions 259 and first pipe 150 and gaps between heat dissipating portions 259 by the circulating flow, third pipe 155 exchanges heat with coolant 10G with heat dissipating portions 259 interposed therebetween. As a result, third pipe 155 directly exchanges heat with coolant 10G and indirectly exchanges heat with coolant 10G with heat dissipating portions 259 interposed therebetween, and is thereby cooled. Coolant 10G that has cooled third pipe 155 is cooled at first refrigeration stage 166, to thereby transport sensible heat.

As described above, heat dissipating portions 259 are provided on at least one of the inner surface of first pipe 150 and the outer surface of third pipe 155 at the coolant container 120 side with respect to first connection portion 171. Therefore, the area of heat exchange with vaporized coolant 10G flowing through first pipe 150 can be increased, to lower the temperature of at least one of first pipe 150 and third pipe 155. That is, the amount of heat entering coolant container 120 from at least one of first pipe 150 and third pipe 155 can be reduced. This, in turn, can improve cooling efficiency in coolant container 120.

Third Embodiment

A superconducting magnet according to a third embodiment of the present invention is described below. The superconducting magnet according to the third embodiment of the present invention is different from superconducting magnet 100 in the configuration of each of the connection pipe and the radiation shield. Thus, description of the configuration similar to that of superconducting magnet 100 according to the first embodiment of the present invention will not be repeated.

Figure 8:
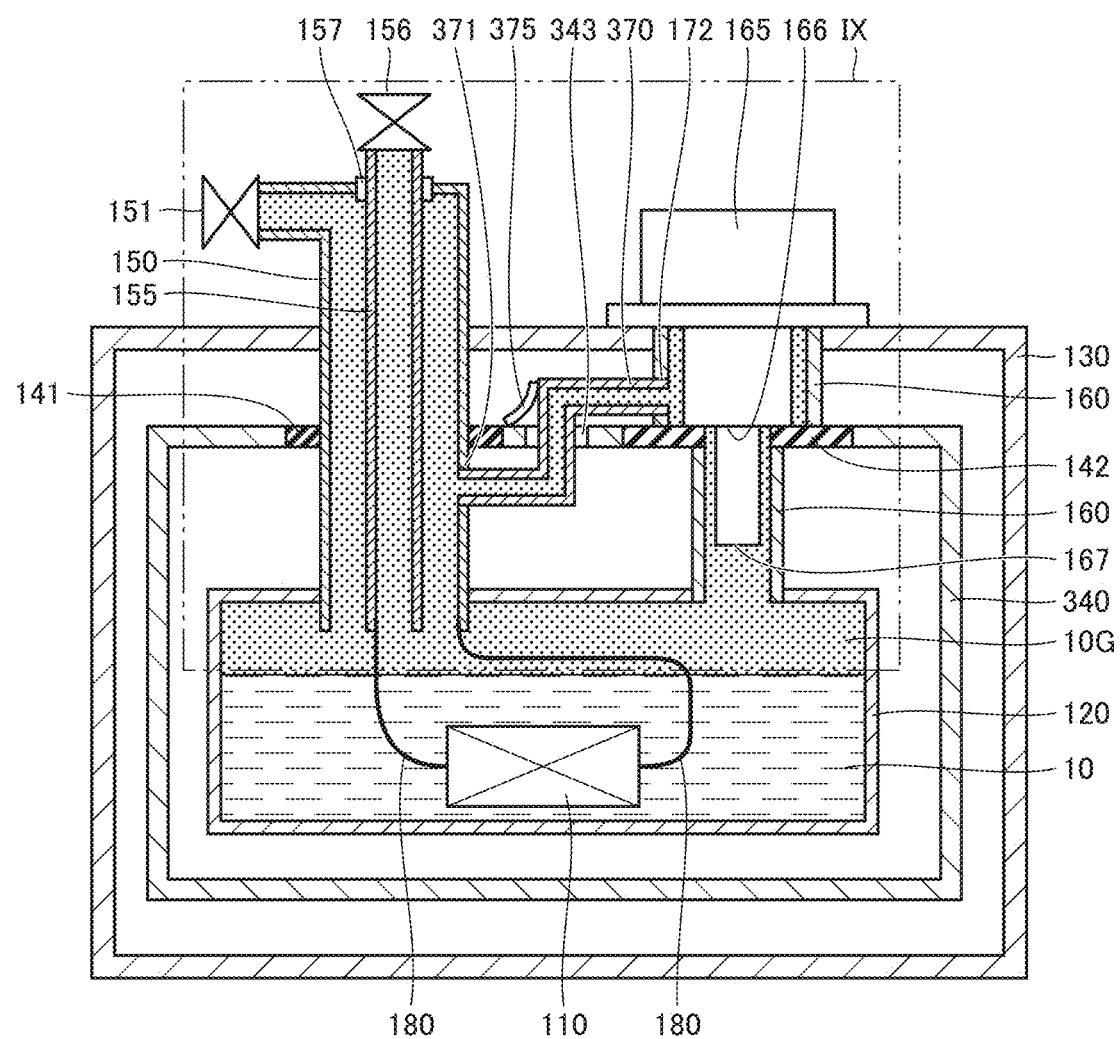
FIG. 8 is a cross-sectional view showing the configuration of a superconducting magnet according to a third embodiment of the present invention.
Figure 9:
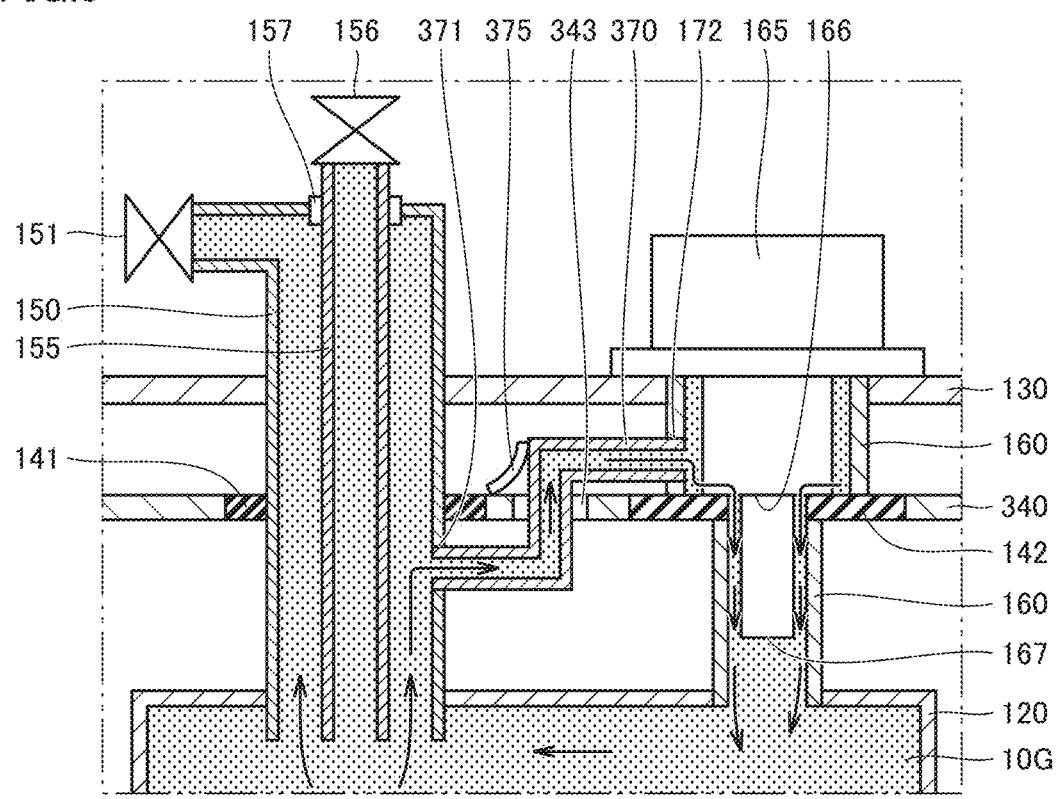
FIG. 9 shows a circulating flow of vaporized coolant, by enlarging a part IX in FIG. 8.

FIG. 8 is a cross-sectional view showing the configuration of the superconducting magnet according to the third embodiment of the present invention. FIG. 9 shows a circulating flow of vaporized coolant, by enlarging a part IX in FIG. 8. FIG. 8 shows a cross section of only the upper part of the superconducting magnet. In FIGS. 8 and 9, the components are shown in a simplified form for the sake of simplicity.

In the superconducting magnet according to the third embodiment of the present invention, as shown in FIGS. 8 and 9, an outer circumferential surface of a connection pipe 370 is indirectly in contact with a radiation shield 340. Specifically, the outer circumferential surface of connection pipe 370 is indirectly in contact with radiation shield 140 with a heat conducting portion 375 interposed therebetween.

In the present embodiment, a first connection portion 371 of connection pipe 370 is located between radiation shield 140 and coolant container 120. Second connection portion 172 of connection pipe 370 is located between vacuum container 130 and radiation shield 340, as in the first embodiment of the present invention. Radiation shield 340 is provided with a through hole 343 at a position between one and the other of the openings.

Connection pipe 370 is provided from first connection portion 371 located between radiation shield 140 and coolant container 120, through through hole 343, to second connection portion 172 located between vacuum container 130 and radiation shield 340.

Heat conducting portion 375 is preferably made of a material having a relatively high thermal conductivity. Heat conducting portion 375 is made of copper, for example. Heat conducting portion 375 is preferably made of a flexible conductor.

Note that heat conducting portion 375 does not necessarily have to be provided, and the outer circumferential surface of connection pipe 370 may be directly in contact with radiation shield 340. In this case, the outer circumferential surface of connection pipe 370 is in contact with an edge of through hole 343 provided in radiation shield 340.

As shown in FIG. 9, in the superconducting magnet according to the present embodiment, a circulating flow of coolant 10G, driven by the density difference in vaporized coolant 10G in second pipe 160, is naturally generated, as in the superconducting magnet according to the first embodiment of the present invention. That is, a circulating flow in which coolant 10G circulates through coolant container 120, first pipe 150, connection pipe 370, second pipe 160 and coolant container 120 in this order is naturally generated. This circulating flow can allow coolant 10G to transport the heat that has entered coolant container 120 to first refrigeration stage 166 of refrigerator 165 by utilizing sensible heat of vaporized coolant 10G. This, in turn, can improve cooling efficiency in coolant container 140.

Further, in the superconducting magnet according to the present embodiment, since the outer circumferential surface of connection pipe 370 is directly or indirectly in contact with radiation shield 340, heat exchange is performed between vaporized coolant 10G flowing through connection pipe 370 and radiation shield 340, with connection pipe 370 interposed therebetween. With this heat exchange, the temperature of radiation shield 340 can be lowered, and accordingly the entry of heat due to radiation from radiation shield 340 to coolant container 120 can be reduced. Accordingly, the amount of heat required to cool the interior of coolant container 120 can be reduced. This, in turn, can further improve cooling efficiency of coolant container 120.

Fourth Embodiment

A superconducting magnet according to a fourth embodiment of the present invention is described below. The superconducting magnet according to the fourth embodiment of the present invention is different from the superconducting magnet according to the third embodiment of the present invention only in the configuration of the first pipe. Thus, description of the configuration similar to that of the superconducting magnet according to the third embodiment of the present invention will not be repeated.

Figure 10:
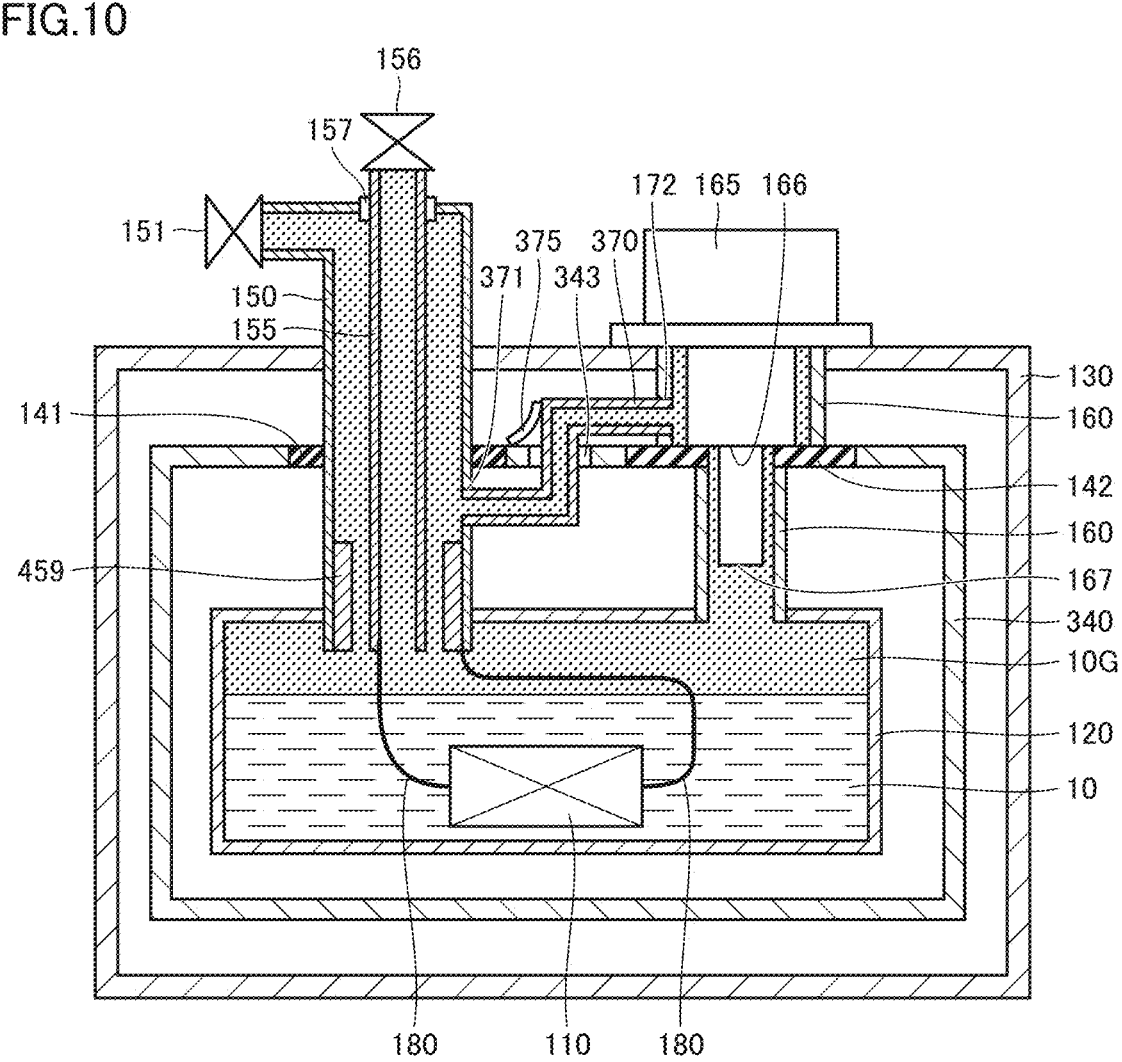
FIG. 10 is a cross-sectional view showing the configuration of a superconducting magnet according to a fourth embodiment of the present invention.

FIG. 10 is a cross-sectional view showing the configuration of the superconducting magnet according to the fourth embodiment of the present invention. FIG. 10 shows a cross section of only the upper part of the superconducting magnet. In FIG. 10, the components are shown in a simplified form for the sake of simplicity.

The superconducting magnet according to the fourth embodiment of the present invention further includes, as shown in FIG. 10, heat dissipating portions 459 provided on the inner surface of first pipe 150 at the coolant container 120 side with respect to first connection portion 371.

Heat dissipating portions 459 are made of, for example, a material having a high thermal conductivity such as copper or aluminum. The superconducting magnet according to the present embodiment includes a plurality of heat dissipating portions 459, as with the superconducting magnet according to the second embodiment of the present invention, which are spaced from one another in the circumferential direction of first pipe 150. The plurality of heat dissipating portions 459 are each spaced from third pipe 155.

When vaporized coolant 10G in first pipe 150 is flowing through a gap between heat dissipating portions 459 and third pipe 155 and gaps between heat dissipating portions 459 by the circulating flow, first pipe 150 exchanges heat with coolant 10G with heat dissipating portions 459 interposed therebetween. As a result, first pipe 150 directly exchanges heat with coolant 10G and indirectly exchanges heat with coolant 10G with heat dissipating portions 459 interposed therebetween, and is thereby cooled. Coolant 10G that has cooled first pipe 150 is cooled at first refrigeration stage 166, to thereby transport sensible heat.

Although not particularly limited, the space between heat dissipating portions 459 and third pipe 155 needs to be such that workability during assembly of the superconducting magnet will not be impaired, and that an insulating distance between first pipe 150 and third pipe 155 can be secured.

Although heat dissipating portions 459 are shaped as fins extending along the direction in which first pipe 150 extends in the present embodiment, the present embodiment is not limited as such. Heat dissipating portions 459 may be provided on the outer surface of third pipe 155, as in the variation of the second embodiment of the present invention.

As described above, heat dissipating portions 459 are provided on at least one of the inner surface of first pipe 150 and the outer surface of third pipe 155 at the coolant container 120 side with respect to first connection portion 371. Therefore, the area of heat exchange with vaporized coolant 10G flowing through first pipe 150 can be increased, to lower the temperature of at least one of first pipe 150 and third pipe 155. That is, the amount of heat entering coolant container 120 from at least one of first pipe 150 and third pipe 155 can be reduced. This, in turn, can improve cooling efficiency in coolant container 120.

Fifth Embodiment

A superconducting magnet according to a fifth embodiment of the present invention is described below. The superconducting magnet according to the fifth embodiment of the present invention is different from superconducting magnet 100 according to the first embodiment of the present invention only in the configuration of the third pipe. Thus, description of the configuration similar to that of superconducting magnet 100 according to the first embodiment of the present invention will not be repeated.

Figure 11:
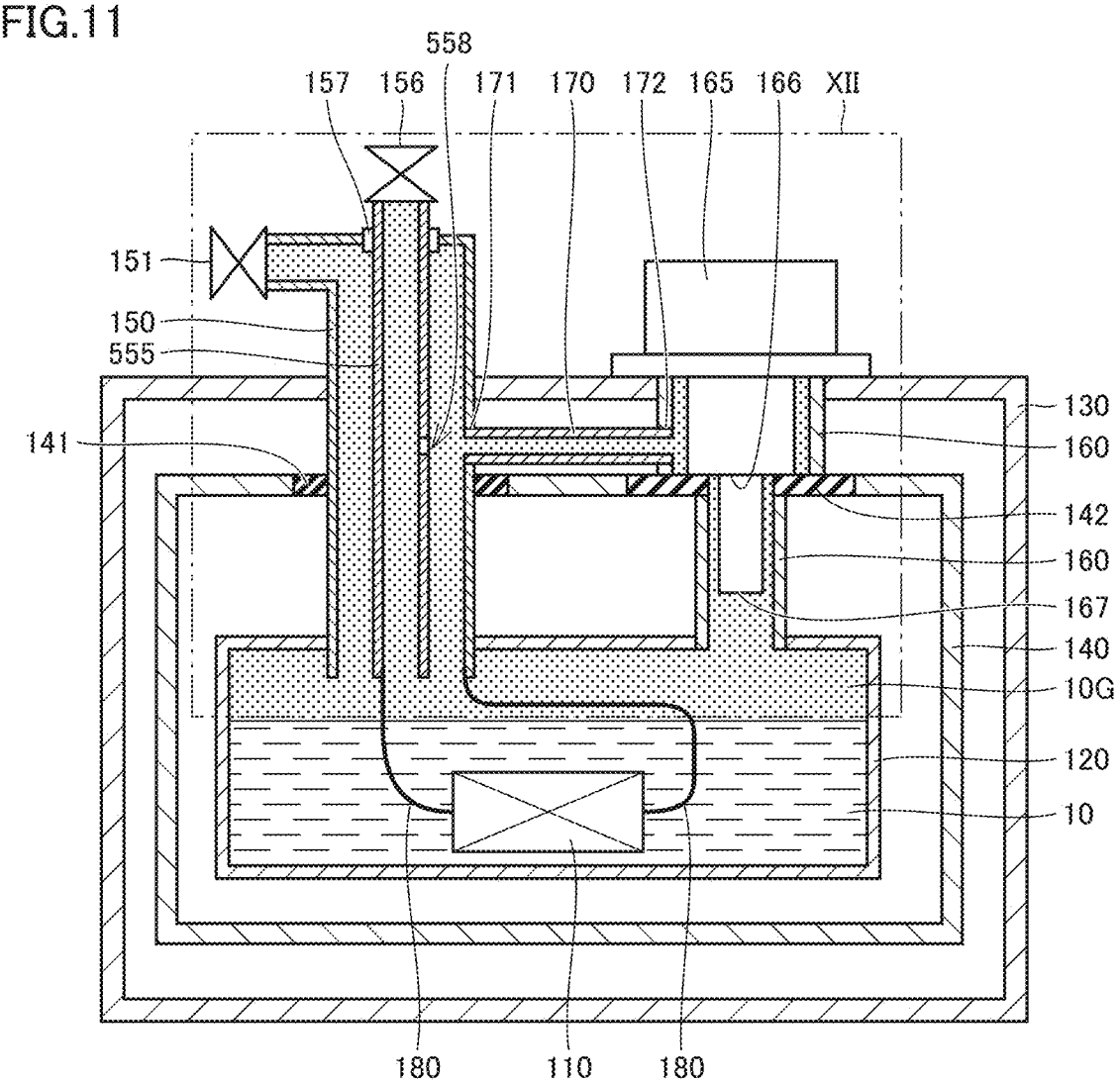
FIG. 11 is a cross-sectional view showing the configuration of a superconducting magnet according to a fifth embodiment of the present invention.
Figure 12:
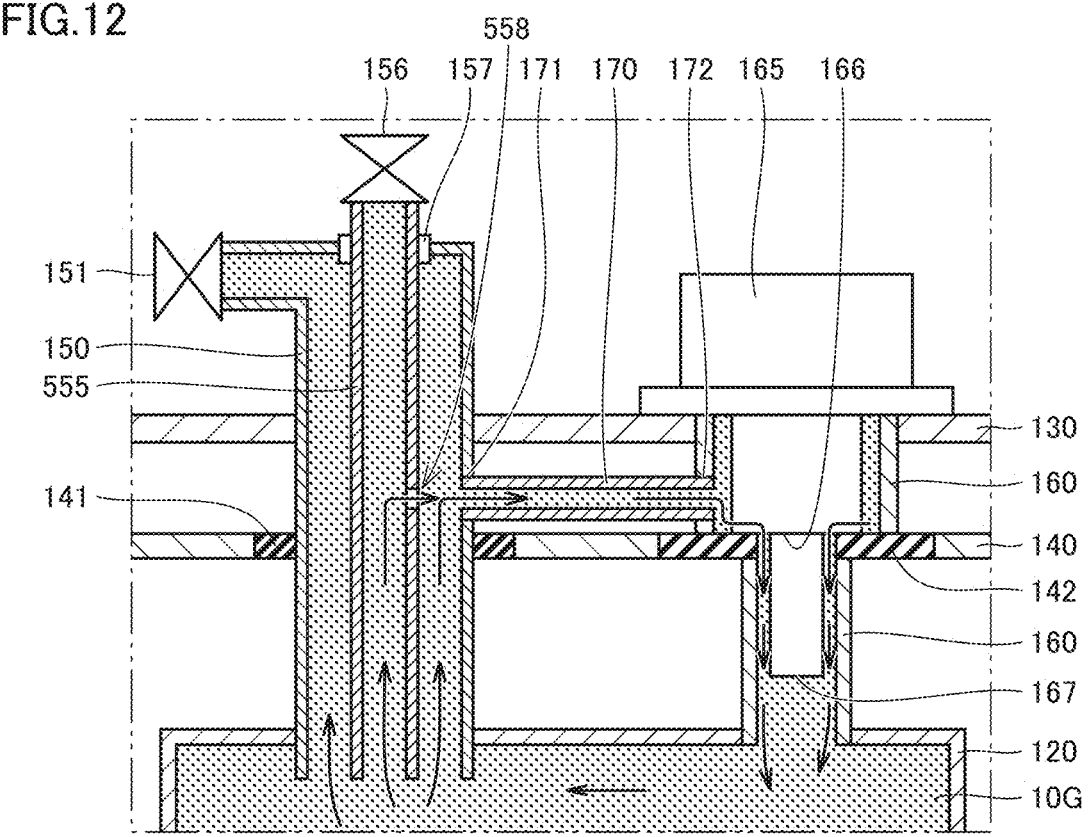
FIG. 12 shows a circulating flow of vaporized coolant, by enlarging a part XII in FIG. 11.

FIG. 11 is a cross-sectional view showing the configuration of the superconducting magnet according to the fifth embodiment of the present invention. FIG. 12 shows a circulating flow of vaporized coolant, by enlarging a part XII in FIG. 11. In FIGS. 11 and 12, the components are shown in a simplified form for the sake of simplicity.

As shown in FIG. 11, in a superconducting magnet 500 according to the fifth embodiment of the present invention, a third pipe 555 has a hole portion 558 connecting the interior and the exterior of third pipe 555.

As shown in FIG. 12, in the present embodiment, coolant 10G generated by vaporization inside coolant container 120 flows between first pipe 150 and third pipe 555, and also flows through third pipe 555, by the circulating flow. As a result, third pipe 555 directly exchanges heat with coolant 10G both outside and inside, and is thereby cooled.

Coolant 10G that has cooled third pipe 555 from inside by flowing through third pipe 555 flows from inside of third pipe 555 to outside of third pipe 555 through hole portion 558. This coolant 10G flows to connection pipe 170 while joining coolant 10G flowing between first pipe 150 and third pipe 555. In this manner, coolant 10G that has cooled first pipe 150 and that has cooled third pipe 555 from both outside and inside flows through connection pipe 170, and is then cooled at first refrigeration stage 166 of refrigerator 165, to thereby transport sensible heat.

In the present embodiment, hole portion 558 is at least partially disposed at a position facing first connection portion 171 of connection pipe 170. Note that the position at which hole portion 558 is disposed is not limited to this position, so long as the position is such that coolant 10G that has flowed through third pipe 555 flows into connection pipe 170 through hole portion 558. Hole portion 558 may be disposed above or below the position facing first connection portion 171. Hole portion 558 does not necessarily have to face first connection portion 171.

Further, although one hole portion 558 is provided in third pipe 555 in the present embodiment, a plurality of hole portions 558 may be provided. The plurality of hole portions 558 may be disposed along a direction in which third pipe 555 extends, or along a circumferential direction of third pipe 555. The size and shape of hole portion 558 are not particularly limited so long as the strength of third pipe 555 is maintained.

As described above, with hole portion 558 provided in third pipe 555, vaporized coolant 10G also flows through third pipe 555 by the circulating flow. Accordingly, the area of heat transfer between coolant 10G and third pipe 555 can be increased while the area of heat transfer between coolant 10G and first pipe 150 is maintained, to lower the temperature of third pipe 555. That is, the amount of heat entering coolant container 120 from each of first pipe 150 and third pipe 555 can be reduced. This, in turn, can improve cooling efficiency in coolant container 120.

The embodiments disclosed herein are illustrative in every respect, and do not serve as a basis for limitative interpretation. Therefore, the technical scope of the present invention should not be interpreted only based on the embodiments described above, but is defined based on the description in the scope of the claims. Further, any modification within the meaning and scope equivalent to the claims is included.

REFERENCE SIGNS LIST 10, 10G: coolant; 100: superconducting magnet; 110: superconducting coil; 120: coolant container; 130: vacuum container; 140, 340: radiation shield; 141: first thermal anchor; 142: second thermal anchor 150: first pipe; 151: first pressure release valve; 155, 555: third pipe; 156: second pressure release valve; 157: insulating portion; 160: second pipe; 165: refrigerator; 166: first refrigeration stage; 167: second refrigeration stage; 170, 370: connection pipe; 171, 371: first connection portion 172: second connection portion; 180: current lead; 259, 459: heat dissipating portion; 343: through hole; 375: heat conducting portion; 558: hole portion.

The invention claimed is:

1. A superconducting magnet comprising:
a superconducting coil;
a coolant container containing the superconducting coil and coolant for cooling the superconducting coil;
a radiation shield disposed between the coolant container and a vacuum container containing the coolant container, to surround the coolant container;
a first pipe connected to the coolant container from outside of the vacuum container;
a second pipe connected to the coolant container from outside of the vacuum container;
a refrigerator fixed to seal a tip end of the second pipe, and inserted in the second pipe to define a flow path of the coolant between the refrigerator and the second pipe; and
a connection pipe to make an interior of the first pipe and an interior of the second pipe communicate with each other inside the vacuum container,
the connection pipe including a first connection portion connecting to the first pipe and a second connection portion connecting to the second pipe, and
the second connection portion being located between the vacuum container and the radiation shield.

2. The superconducting magnet according to claim 1, wherein
the refrigerator includes a first refrigeration stage and a second refrigeration stage,
the first refrigeration stage is located in a region between the vacuum container and the radiation shield inside the second pipe, and
the second refrigeration stage is located in at least one of a region between the radiation shield and the coolant container inside the second pipe, and an upper region inside the coolant container.

3. The superconducting magnet according to claim 2, wherein
the first refrigeration stage is located in a region between the second connection portion and the radiation shield inside the second pipe.

4. The superconducting magnet according to claim 1, further comprising a third pipe extending from outside of the vacuum container toward the coolant container and at least partially extending along the first pipe while being spaced from the first pipe inside the first pipe.

5. The superconducting magnet according to claim 4, further comprising a heat dissipating portion provided on at least one of an inner surface of the first pipe and an outer surface of the third pipe at a coolant container side with respect to the first connection portion.

6. The superconducting magnet according to claim 4, wherein
the third pipe has a hole portion connecting an interior and an exterior of the third pipe, and
the interior of the third pipe and an interior of the connection pipe communicate with each other through the hole portion.

7. The superconducting magnet according to claim 1, wherein
an outer circumferential surface of the connection pipe is directly or indirectly in contact with the radiation shield.

* * * * *